(12) United States Patent
Thompson

(10) Patent No.: US 10,383,842 B2
(45) Date of Patent: Aug. 20, 2019

(54) METHOD AND COMPOSITION FOR PREVENTING AND TREATING VIRAL INFECTIONS

(71) Applicant: Daryl Thompson, Winter Haven, FL (US)

(72) Inventor: Daryl Thompson, Winter Haven, FL (US)

(73) Assignee: GLOBAL BIOLIFE INC., Bethesda, MD (US)

( * ) Notice: Subject to any disclaimer, the term of this patent is extended or adjusted under 35 U.S.C. 154(b) by 0 days.

(21) Appl. No.: 15/043,472

(22) Filed: Feb. 12, 2016

(65) Prior Publication Data

US 2016/0367517 A1 Dec. 22, 2016

Related U.S. Application Data

(60) Provisional application No. 62/115,983, filed on Feb. 13, 2015.

(51) Int. Cl.
| | | |
|---|---|---|
| *A61P 31/16* | (2006.01) | |
| *A61K 9/00* | (2006.01) | |
| *A61K 9/20* | (2006.01) | |
| *A61K 9/48* | (2006.01) | |
| *A61K 47/16* | (2006.01) | |
| *A61K 47/22* | (2006.01) | |
| *A61K 31/352* | (2006.01) | |
| *A61K 31/353* | (2006.01) | |

(52) U.S. Cl.
CPC .......... *A61K 31/352* (2013.01); *A61K 9/0019* (2013.01); *A61K 9/2013* (2013.01); *A61K 9/4858* (2013.01); *A61K 31/353* (2013.01); *A61K 47/16* (2013.01); *A61K 47/22* (2013.01); *A61P 31/16* (2018.01)

(58) Field of Classification Search
CPC .. A61K 31/352; A61K 31/353; A61K 9/4858; A61K 9/2013; A61K 9/0019; A61K 47/16; A61K 47/22; A61P 31/16
See application file for complete search history.

(56) References Cited

U.S. PATENT DOCUMENTS

2012/0022010 A1 * 1/2012 Brand .................. A61K 31/352
514/27

OTHER PUBLICATIONS

Anderson et al., Peptides, 2003, 24, p. 487-501.*
Von Itzstein, M., Nature Reviews: Drug Discovery, 2007, 6, p. 967-974.*
Definition of prevent, Oxford English Dictionary Online, http://dictionary.oed.com/, accessed online Mar. 27, 2010, especially definition 9a. at p. 2.*
Overview of Viruses, The Merck Manual, http://www.merckmanuals.com, accessed online Jul. 3, 2017, Last full review/revision Aug. 2013.*
Feng et al., Molecules, 2014, 19, p. 5624-5633, published Apr. 30, 2014.*
Seo et al., Food Control, 2016, 60, p. 25-30. (Year: 2016).*

* cited by examiner

*Primary Examiner* — Jonathan S Lau
(74) *Attorney, Agent, or Firm* — Stephen J. Weyer, Esq.; Stites & Harbison, PLLC

(57) ABSTRACT

A method and composition for treating viral infections using a combination of naturally occurring compounds is provided. The method includes administering to a patient at risk of or diagnosed with a viral infection a composition including therapeutically effective amounts of a helicase ATPase inhibitor, a sialidase enzyme inhibitor, and ICAM-1 inhibitor which each also down regulate the immune response. The composition may further include a permeation enhancer.

7 Claims, No Drawings

METHOD AND COMPOSITION FOR PREVENTING AND TREATING VIRAL INFECTIONS

RELATED APPLICATIONS

This application claims priority to U.S. Provisional Application No. 62/115,983 filed Feb. 13, 2015. The entire contents of the above application are hereby incorporated by reference as though fully set forth herein.

FIELD

The present disclosure relates generally to preventing and treating viral infections, and more particularly to a composition including a helicase ATPase inhibitor, a sialidase enzyme inhibitor, an ICAM-1 Inhibitor and TNF-a inhibitor to down regulate the immune cytokine response, administered to a patient at risk of or diagnosed with a viral infection.

BACKGROUND

Many human diseases result from infection by microscopic organisms called viruses. Infection by viruses can give rise to symptoms that vary from mild to severe. Viral infections can result in large numbers of deaths. Examples of such pandemics include the Spanish flu of 1918-1919 that killed approximately 40 million people and the HIV/AIDS epidemic that has killed almost 2 million people.

Viruses require host organisms in order to replicate and viruses are transmitted from an infected host to an uninfected host through a number of mechanisms. A virus will first attach itself to a host cell. It will then enter the cell and release its genetic code (i.e., RNA or DNA). The virus makes use of the host cell's functional proteins and enzymes in order to replicate. Eventually, the host cell may die because the mechanisms it needs to survive are controlled by the virus. After death of the cell, the replicated viruses are released, allowing them to attack new host cells and continuing the replication process. Some viruses cause modification of the host cells leading to cancer, while other viruses can remain dormant in the host for an extended period prior to the infection becoming symptomatic in the host.

The symptoms that result from viral infections can vary from virus-to-virus as any one virus typically will infect only certain types of cells. This observation also means that a specific virus will typically infect only certain species, although mutation of a virus can allow it to extend the number of species that any one virus is able to infect.

Host species have developed a number of defense mechanisms to protect themselves from viral infections. The first lines of defense are mechanisms that prevent viral entry into the host. The skin provides an impermeable barrier to entry. Viruses typically enter the body through body cavities and can pass through the mucosal surfaces that line these cavities. Once a virus is in the body and detected by the body's immune system, lymphocytes and monocytes in the blood learn how to attack the invader. Invaded cells release cytokines such as the interferons (for example IL 1, IL 6, IL 12, IL 16), tumor necrosis factor (TNF-a), and interferons (typically interferons a and g). The role of these cytokines is to increase the resistance of other host cells to the invading virus. Many of the symptoms of viral infection experienced by the host results from the extensive release of cytokines, commonly referred to as the cytokine storm.

The white blood cells are able to remember how to combat viruses that have previously invaded the body. So if the host survives the initial attack of the virus, the immune system is able to respond much more quickly to subsequent infections of the same virus. The body has developed an immunity to the virus. Such immunity can also be induced by presenting the immune system with a surrogate (vaccine) for the virus in a process known as immunization.

Antiviral drugs are known in the art to assist the immune system in overcoming a viral infection in a patient. Most antiviral drugs work by slowing the replication of the virus in the infected patient's body thus allowing the body's immune system to launch an effective response when the disease symptoms are less severe. Antiviral drugs may work specifically on one or two viruses or may be effective across a broad spectrum of viruses. There are many known mechanisms by which antiviral agents can slow viral replication. One antiviral strategy is to slow or prevent the virus infiltrating a target cell, for example by binding to a receptor on the target cell which is required by the virus to enter the cell or by coating the virus so preventing its ability to bind to the target receptor(s). Other antiviral agents can slow viral replication once the virus particle has entered the target cell. Such mechanisms are well known in the art.

BRIEF SUMMARY OF THE INVENTION

The present invention provides a method and composition for treating viral infections using a combination of naturally occurring compounds. In one embodiment, the method includes administering to a patient at risk of or diagnosed with a viral infection a composition including therapeutically effective amounts of a helicase ATPase inhibitor, a sialidase enzyme inhibitor and ICAM-1 inhibitor. The composition may further include a permeation enhancer.

The composition is effective in combating a viral infection by reducing replication rates for the virus and by reducing the virus's ability to stimulate the immune response of the host, thereby preserving cellular integrity. Specifically, the composition is effective in inhibiting the ATPase activity of the replication enzyme helicase on the cell surface by docking site competition. Moreover, the composition is effective in inhibiting the sialidase and ICAM-1 enzymes, which are involved in the entry and release stages of intercellular virus particles.

In one aspect of the invention there is provided a method of preventing and treating viral infections including administering a composition including therapeutically effective amounts of a helicase ATPase inhibitor, a sialidase enzyme inhibitor and ICAM-1 inhibitor to a patient at risk of or diagnosed with a viral infection.

In another aspect of the invention there is provided a composition for treating viral infections including therapeutically effective amounts of a helicase ATPase inhibitor, a sialidase enzyme inhibitor and ICAM-1 Inhibitor.

In one embodiment, the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

In another embodiment, the helicase ATPase inhibitor includes a naturally occurring compound, a synthetic derivative of a naturally occurring compound or a combination thereof.

In another embodiment, the naturally occurring ATPase inhibitor compound includes a flavonoid, a flavonoid derivative or a combination thereof.

In another embodiment, the flavonoid ATPase inhibitor is myricetin.

In another embodiment, the I-CAM 1 inhibitor includes a flavonoid, a flavonoid derivative or a combination thereof.

In another embodiment, the ICAM-1 inhibitor is myricetin.

In another embodiment, the sialidase enzyme inhibitor includes a naturally occurring compound, a synthetic derivative of a naturally occurring compound or a combination thereof.

In another embodiment, the naturally occurring sialidase enzyme inhibitor compound includes a flavonoid, a flavonoid derivative or a combination thereof.

In another embodiment, the flavonoid sialidase enzyme inhibitor is hesperitin or hesperidin.

In another embodiment, the viral infection is the Ebola virus.

In another embodiment, the patient is a human.

In another embodiment, the composition further includes a permeation enhancer.

In another embodiment, the permeation enhancer is piperine.

In another embodiment, the helicase ATPase and ICAM-1 inhibitor is myricetin and the sialidase enzyme inhibitor is hesperitin.

In another embodiment, the composition further includes piperine.

In another embodiment, about 300 to about 700 mg myricetin; about 100 to about 500 mg hesperitin; and about 5 to about 100 mg piperine are present in the composition.

In another embodiment, about 450 to about 600 mg myricetin; about 250 to about 400 mg hesperitin; and about 5 to about 50 mg piperine are present in the composition.

In another embodiment, about 55 to about 75% weight myricetin; about 30 to about 50% hesperitin; and about 0.5 to about 5% piperine, based on the total weight of the mixture, is present in the composition.

In another embodiment, the ratio of piperine, myricetin and hesperitin present in the composition is about 1:(30-60):(30-60).

In another aspect of the invention there is provided a method of preventing and treating the Ebola virus in a human including administering a composition including 60% myricetin, 39% hesperitin and 1% piperine, based on the total weight of the mixture, to a human at risk of or diagnosed with a the Ebola virus.

In another aspect of the invention there is provided a composition for preventing and treating the Ebola virus including 60% myricetin, 39% hesperitin and 1% piperine, based on the total weight of the mixture.

DETAILED DESCRIPTION

As used herein, the following terms and phrases shall have the meaning set forth below.

The phrase "naturally occurring" when referring to a compound means a compound that is in a form in which it can be found naturally. A compound is not in a form that is naturally occurring if, for example, the compound has been purified and separated from at least some of the other molecules that are found with the compound in nature. A "naturally occurring compound" refers to a compound that can be found in nature, i.e., a compound that has not been created or modified by man.

"Treating" a condition or disease refers to curing as well as ameliorating at least one symptom of the condition or disease.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the patient and disease or condition being treated, the weight and age of the patient, the severity of the disease or condition, the manner of administration and the like, which can readily be determined by one or ordinary skill in the art. For example, certain compositions described herein may be administered in a sufficient amount to produce a desired effect at a reasonable benefit/risk ratio applicable to such treatment.

The term "pharmaceutically acceptable carrier" means a carrier or diluent that does not give a stimulus to an organism and destroy the natures and bioactivities of an administered compound.

The present invention is directed to administering a composition comprising therapeutically effective amounts of a helicase ATPase inhibitor, a sialidase enzyme inhibitor and ICAM-1 inhibitor to a patient at risk of or diagnosed with a viral infection.

In one embodiment, the effective concentration for a composition consisting of a mixture by weight of a helicase ATPase inhibitor, a sialidase enzyme inhibitor and ICAM-1 inhibitor ranges from about 250 mg to about 1000 mg of the composition. In one embodiment, a single dose per day, taken at the beginning of the day, is about 750 mg, or about 1500 mg. In another embodiment, the composition is administered as a dose three times a day in an amount of about 750 mg per dose. The total amount of the composition administered daily, in one embodiment is at least 500 mg, or at least 750 mg, or at least 1000 mg or at least 2500 mg.

The helicase ATPase inhibitor of the present invention functions as a cellular replication inhibitor by inhibiting the ATPase activity of the replication enzyme helicase on the cell surface by docking site competition. This inhibition reduces viral un-packaging and replication rates and reduces mutation of viral strain due to the inhibiting activity taking place outside the cell.

In one embodiment, the helicase ATPase inhibitor includes a naturally occurring compound, a synthetic derivative of a naturally occurring compound or a combination thereof. There are several naturally occurring compounds that have an effect on viral infections.

In one embodiment, the naturally occurring ATPase inhibitor compound comprises a flavonoid, a flavonoid derivative or a combination thereof. Flavanoids are naturally-occurring antioxidant compounds for which several therapeutic uses have been demonstrated including diabetes, neurological disorders, thrombin inhibition, cancer, and antivirals. Generally, flavonoids generate few side-effects when administered and can safely be provided to patients in large doses. Two types of flavonoids that are useful are flavanones and flavones. Flavanones have the structure (I) shown below and flavones have the similar structure (II) shown below:

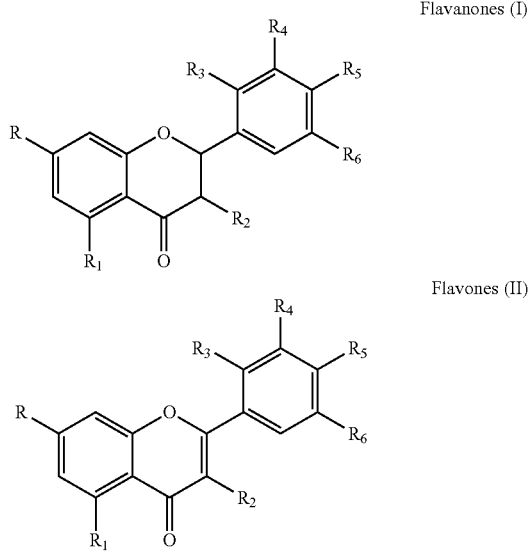

Flavanones (I)

Flavones (II)

wherein R, R1, R2, R3, R4, R5 and R6 are each independently hydrogen, a hydroxy group, an alkoxy group, a rutinosyl group, a rhamnosyl group, a substituted alkoxy group or a substituted acyloxy group wherein the substituent is chosen from hydroxyl, alkoxy, aryloxy, phenyl, halogen, and amido group. Several examples of the flavonoids of formula (I) and (II) are shown below in Table 1.

TABLE 1

|  | R | $R_1$ | $R_2$ | $R_3$ | $R_4$ | $R_5$ | $R_6$ |
|---|---|---|---|---|---|---|---|
| FLAVONE | | | | | | | |
| Flavone | H | H | H | H | H | H | H |
| Chrysin | OH | OH | H | H | H | H | H |
| Apigenin | OH | OH | H | H | H | OH | H |
| Luteolin | OH | OH | H | H | H | OH | H |
| Diosmin | -O-rutinose | OH | H | H | OH | $OCH_3$ | H |
| Fisetin | OH | H | OH | H | OH | OH | H |
| Kaempferol | OH | OH | OH | H | H | OH | H |
| Morin | OH | OH | OH | OH | H | OH | H |
| Quercetin | OH | OH | OH | H | OH | OH | H |
| Myricetin | OH | OH | OH | H | OH | OH | OH |
| Rutin | OH | OH | -O-rutinose | H | OH | OH | H |
| Rhoifolin | R-G-[a] | OH | H | H | H | OH | H |
| FLAVANONE | | | | | | | |
| Galangin | OH | OH | OH | H | H | H | H |
| Hesperetin | OH | OH | H | H | OH | $OCH_3$ | H |
| Eriodictyol | OH | OH | H | H | OH | OH | H |
| Naringenin | OH | OH | H | H | H | OH | H |
| Naringin | R-G-[a] | OH | H | H | H | OH | H |
| Neohesperidin | R-G-[b] | OH | H | H | OH | $OCH_3$ | H |
| Hesperidin | R-G-[b] | OH | H | H | OH | $OCH_3$ | H |
| Narirutin | R-G-[b] | OH | H | H | H | OH | H |
| Prunin | Glucose- | OH | H | H | H | OH | H |

[a] rhamnose-glucose, L-rhamnose is linked α 1→2 to D-glucose
[b] rhamnose-glucose, L-rhamnose is linked α 1→6 to D-glucose In one embodiment, the helicase ATPase inhibitor is the flavonoid myricetin.

Myricetin is a flavonoid found in most berries, including cherry, cranberry and bilberry, and other plants, including parsley and rutabagas. In addition to inhibiting the enzyme helicase, myricetin functions as a powerful and broad cytokine signaling inhibitor and immune-modulator. Myricetin down-regulates cytokine activity and TNF-A. This includes, for example, lymphokines, interleukines and chemokines, particularly interleukins IL-IL-36 and TNF-A.

Naturally occurring flavonoids, such as myricetin, are commonly substituted at variable positions, mainly by hydroxyl, methoxyl, isoprenyl and glycosyl groups. The introduction of halogens in these molecules show strong biological activities, including antiviral properties.

The ICAM-1 inhibitor of the present invention functions to slow viral replication inside the cell by inhibiting the ICAM-1 enzyme, which is involved in entry and release stages of intercellular virus particles.

In one embodiment, the ICAM-1 inhibitor is the flavonoid myricetin.

The sialidase of the present invention functions to slow viral replication inside the cell by inhibiting the sialidase enzyme, which is involved in entry and release stages of intercellular virus particles.

In one embodiment, the sialidase enzyme inhibitor comprises a naturally occurring compound, a synthetic derivative of a naturally occurring compound or a combination thereof. In another embodiment, the naturally occurring sialidase enzyme inhibitor compound comprises a flavonoid, a flavonoid derivative or a combination thereof.

In one embodiment, the sialidase enzyme inhibitor is the flavonoid hesperitin or hesperidin. Hesperidin is a flavonoid found in plants, mainly in citrus fruit peels.

Hesperitin is the aglycone form of hesperidin. In addition to inhibiting the sialidase enzyme, hesperitin and hesperidin function as cellular integrity agents by inhibiting cellular stratum acidification due to excessive histamine and histadine concentrations. Hesperitin and hesperidin further prevent integrin loss by inhibition of intracellular H2O2 production as well as activation of nuclear factor kB, phosphorylation of IkB(alpha), and inhibition of P-38 MAPK (mitogen activated kinase). Hesperitin and hesperidin further enhance cellular integrity by stimulating fibroblast collagen synthesis with associated enhancement of migration and proliferation.

There are several methods by which myricetin, hesperitin or hesperidin may be harvested from their original botanical sources. In one method, for example, extraction from botanical sources begins with a suitable seed material such as grape seeds or tomato seeds, pine bark or citrus rinds. The source material is macerated and flushed with water to separate the water soluble flavonoids from the bulkier pectins and fibers of the source material. This pulp wash is then treated with appropriate acids and bases as known in the art to cause precipitation. The precipitate is then washed again, dried and then concentrated to yield a fairly pure flavonoid composition. This composition may be further clarified to yield fractions containing the desired flavonoid product.

In another method, reverse osmosis may be used to remove the target flavonoid by filtering it out of juice streams from beverage manufacturing processes. The process of manufacturing fruit juices such as citrus, liberates the flavonoids from the rind and suspends them in the juice product. It is often desirable to remove these water soluble flavonoids because of their tendency to produce bitter or off flavors in the juice product.

For example, during the manufacture of grapefruit juice, the primary grapefruit flavonoid naringin is released into the juice stream. Because naringin has a very distinct bitter taste, it is necessary to remove it from the product stream via the use of resin coated reverse osmosis devices to restore the proper flavor profile of the grapefruit juice. The resultant flavonoid is finally collected and dried to yield a fairly pure product.

The flavonoids may also be manufactured by synthetic methods. Such methods may include an Allan-Robinson Reaction, which is a chemical reaction of o-hydroxylaryl ketones with aromatic anhydrides to form flavanones. Another example is Auwers Synthesis, which is a procedure that requires an acid catalyzed aldol condensation between benzaldehyde and a 3-oxypentanon to an o-hydroxychalcone. Further bromination of the alkene group gives a dibromo-adduct that rearranges to a flavanol by reaction with potassium hydroxide. A further example is a Baker-Venkataraman Rearrangement, which involves the reaction of 2-acetoxyacetophenones with base to form 1,3-diketones. The rearrangement reaction proceeds via enolate formation followed by an acyl transfer to form flavanones. An Algar-Flynn-Oyamada Reaction may also be used. In this reaction, a chalcone undergoes an oxidative cyclization to form a flavanol.

The present invention prevents and treats a wide variety of virus infections including, but not limited to Cowpoxvirus, Herpesviridae, Herpes simplex viruses, Epstein-Barr virus, human adenoviruses, human papillomaviruses, hepatitis B virus, Retroviridae (such as human immunodeficiency virus), rotavirus, Filoviridae (such as Marburg virus and Ebola viruses), Dengue virus, influenza viruses, hanta virus, Severe acute respiratory syndrome coronavirus, Entero viruses, Rhino virus, Hepatitis virus, Norovirus, Norwalk virus, Alpha viruses, Chikungunya virus, Venezuelan equine encephalitis virus, Western equine encephalitis virus, Eastern equine encephalitis virus, St. Louis encephalitis virus, West Nile virus, Yellow fever virus, and Creutzfeldt-Jakob-Disease, Arbovirus, Flavivirus and RNA viruses.

In one embodiment, the viral infection is the Ebola virus. Viral Ebola's lethality is caused by the virus's ability to over stimulate the host's autoimmune response. The resulting saturation of the host's cytokine chemicals causes rapid cell adhesion loss due to the cytokine's destabilizing activity on integrin. The result is loss in cellular integrity and finally fatal hemorrhaging of vascular tissues and organs.

Ebola accomplishes this by secreting specific glycolproteins (e.g., secreted glyol-protein (sGP)) that interact with specific receptors on the cell surface to stimulate immune signaling response. The over-signaling initiates a cytokine response, which in turn initiates chemokine release. The resulting and overwhelming concentration of chemokines leads to integrin loss at the cellular level.

The present invention combats the Ebola virus by reducing replication rates for the virus and reducing the virus's ability to stimulate the immune response of the host, thereby preserving cellular integrity.

The composition of the present invention may be administered to patients at risk of viral infection, for example through exposure to patients known or suspected of having a viral disease, in order to prevent or lessen the severity of symptoms following infection and/or reduce the possibility of severe symptoms or death following infections.

The composition of the present invention may be administered to patients known or suspected of having a viral disease, in order to lessen the severity of symptoms and/or reduce the possibility of severe symptoms or death.

In one embodiment, the patient is a human. In other embodiments, the patient may be a mammal other than a human, such as a dog.

In one embodiment, the composition further includes a permeation enhancer. The permeation enhancer of the present invention functions to enhance oral uptake or cellular uptake of the helicase ATPase inhibitor, ICAM-1 enzyme inhibitor and the sialidase enzyme inhibitor.

In one embodiment, the permeation enhancer is piperine. Piperine is an alkaloid and is responsible for the pungency of black pepper and long pepper. Piperine is commercially available or may be extracted from black pepper using dichloromethane. Piperine increases the bioavailability of nutrients.

In one embodiment, the helicase ATPase inhibitor and ICAM-1 inhibitor is myricetin, the sialidase enzyme inhibitor is hesperitin and the composition further includes piperine. In one embodiment, the composition includes about 300 to about 700 mg myricetin; about 100 to about 500 mg hesperitin; and about 5 to about 100 mg piperine. In another embodiment, the composition includes about 450 to about 600 mg myricetin; about 250 to about 400 mg hesperitin; and about 5 to about 50 mg piperine.

In one embodiment, the composition includes a mixture of about 50 to about 80% weight myricetin; about 25 to about 55% hesperitin; and about 0.5 to about 10% piperine, based on the total weight of the mixture. In another embodiment, the composition includes a mixture of about 55 to about 75% weight myricetin; about 30 to about 50% hesperitin; and about 0.5 to about 5% piperine, based on the total weight of the mixture. In yet another embodiment, the composition includes a mixture of about 60% myricetin; about 39% hesperitin; and 1% piperine, based on the total weight of the mixture.

In one embodiment, the composition includes a ratio of piperine to myricetin to hesperitin of about 1:(2-4):(2-4), or about 1:(2-3):(2-3), or about 1:3:3. In another embodiment, the composition includes a ratio of piperine to myricetin to hesperitin of about 1:(20-75):(20-75), or about 1:(30-60):(30-60), or about 1:(40-55):(40-55).

In one embodiment, the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

Formulations of the invention suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, each containing a predetermined amount of a compound of the present invention as an active ingredient.

In solid dosage forms of the invention for oral administration, the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents.

Embodiments of inventive compositions and methods are illustrated in the following examples. These examples are provided for illustrative purposes and are not considered limitations on the scope of inventive compositions and methods.

EXAMPLES

Example 1

A gelatin capsule containing 300 mg myricetin, 195 mg hesperitin and 5 mg piperine is administered orally to a patient twice a day, taken with food.

Example 2

A tablet containing sodium citrate, 500 mg myricetin, 300 mg hesperitin and 10 mg is administered orally once a day upon rising.

Example 3

A powder containing 600 mg myricetin, 390 mg hesperitin and 10 mg piperine is sprinkled onto foods such as, for example scrambled eggs after cooking but prior to consumption.

Example 4

A composition containing a blend of 55% by weight myricetin, 35% by weight hesperitin and 10% by weight piperine is blended into a saline solution and is injected intravenously, such that there is 1 mg of the composition per 1 g of saline solution.

For the purposes of promoting an understanding of the principles of the invention, the invention has been explained in relation to various embodiments, it is to be understood that various modifications thereof will be apparent to those skilled in the art upon reading the specification. The features of the various embodiments of the articles described herein may be combined within an article. Therefore, it is to be understood that the invention described herein is intended to cover such modifications as fall within the scope of the appended claims.

What is claimed is:

1. A method of limiting the occurrence of, reducing the risk or severity of or treating influenza infections comprising administering a composition consisting of therapeutically effective amounts of myricetin and hesperitin to a patient at risk of or diagnosed with influenza.

2. The method of claim 1, wherein the composition is administered to the patient by oral administration, intravenous injection, intramuscular injection, intrathecal injection, subcutaneous administration, sublingually, buccal administration, rectal administration, vaginal administration, ocular administration, otic administration, nasal administration, inhalation through the mouth, inhalation through the nose, transdermally or any combination thereof.

3. The method according to claim 1, wherein the patient is a human.

4. The method claim 1, wherein about 300 to about 700 mg myricetin and about 100 to about 500 mg hesperitin are present in the composition.

5. The method of claim 1, wherein about 450 to about 600 mg myricetin and about 250 to about 400 mg hesperitin are present in the composition.

6. The method of claim 1, wherein about 55 to about 75% weight myricetin and about 30 to about 50% hesperitin based on the total weight of the mixture, is present in the composition.

7. The method of claim 1, wherein the ratio of myricetin to hesperitin present in the composition is about (30-60):(30-60).

* * * * *